United States Patent

Yanof et al.

[11] Patent Number: 6,052,611
[45] Date of Patent: Apr. 18, 2000

[54] FRAMELESS STEREOTACTIC TOMOGRAPHIC SCANNER FOR IMAGE GUIDED INTERVENTIONAL PROCEDURES

[75] Inventors: Jeffrey H. Yanof, Solon; Joseph S. Deucher, Lyndhurst; Fred C. Jensen, Chagrin Falls; Anton Z. Zupancic, Kirtland; Henry S. Novak, Richfield; Karl J. West, Painesville, all of Ohio

[73] Assignee: Picker International, Inc., Highland Heights, Ohio

[21] Appl. No.: 08/980,382

[22] Filed: Nov. 28, 1997

[51] Int. Cl.[7] .................................................. A61B 19/00
[52] U.S. Cl. .......................... 600/429; 606/130; 378/207
[58] Field of Search ................................. 600/429, 417; 606/130; 378/205–207, 20; 395/80, 86, 89; 901/2, 3

[56] References Cited

U.S. PATENT DOCUMENTS

| | | | |
|---|---|---|---|
| 4,791,934 | 12/1988 | Brunnett | 128/653 |
| 5,078,140 | 1/1992 | Kwoh | 128/653.1 |
| 5,099,846 | 3/1992 | Hardy | 128/653.1 |
| 5,142,930 | 9/1992 | Allen et al. | 74/469 |
| 5,230,338 | 7/1993 | Allen et al. | 128/653 |
| 5,309,913 | 5/1994 | Kormos et al. | 128/653.1 |
| 5,327,474 | 7/1994 | Inoue et al. | |
| 5,345,540 | 9/1994 | Schleifer et al. | |
| 5,398,684 | 3/1995 | Hardy | 128/653.1 |
| 5,441,505 | 8/1995 | Nakamura | |
| 5,494,034 | 2/1996 | Schlondorff et al. | |
| 5,524,180 | 6/1996 | Wang et al. | 600/118 |
| 5,528,116 | 6/1996 | Snell | |
| 5,533,082 | 7/1996 | Grönemeyer et al. | 378/20 |
| 5,590,655 | 1/1997 | Hussman | 128/653.1 |
| 5,598,269 | 1/1997 | Kitaevich et al. | 356/399 |
| 5,622,170 | 4/1997 | Schulz | 128/653.1 |
| 5,628,327 | 5/1997 | Unger, et al. | 128/749 |
| 5,647,373 | 7/1997 | Paltieli | 128/749 |
| 5,657,429 | 8/1997 | Wang et al. | 395/86 |
| 5,682,890 | 11/1997 | Kormos et al. | |
| 5,823,960 | 10/1998 | Young et al. | |
| 5,921,992 | 7/1999 | Costales et al. | |
| 5,923,727 | 7/1999 | Navab | |

FOREIGN PATENT DOCUMENTS 2 094 590   9/1982   United Kingdom .

Primary Examiner—William E. Kamm
Assistant Examiner—Shawna J Shaw
Attorney, Agent, or Firm—Fay, Sharpe, Fagan, Minnich & McKee, LLP

[57] ABSTRACT

A frameless stereotactic tomographic scanner includes an imaging device defining a coordinate system in scanner space (Π). A localizer device includes a base portion mounted in a fixed relationship to the imaging device and a free end adapted for selective movement into varied positions near a patient body disposed on the imaging device. A position transducer associated with the localizer device generates, in a localizer space (R), localizer device tip location information as the localizer device is moved near the patient body. A localizer space to scanner space transform processor converts the localizer tip location information to converted localizer tip location information in an image space (I). The imaging device is adapted to generate patient body image information in the image space (I) regarding the patient body disposed on the device. A display unit is included for displaying the patient body image information together with the localizer tip position information on a human readable display monitor. The base portion of the localizer device is adapted for mounting onto the imaging device at a plurality of fixed positions. The imaging device includes an overhead track assembly defining the set of fixed localizer device positions. A calibration phantom is provided including a set of imagable touch point sites for generating a localizer space to scanner space vector based on a pair of centroids developed in the scanner space (TT) and the localizer space (RR) during a calibration and verification process.

20 Claims, 9 Drawing Sheets

FRAMELESS STEREOTACTIC TOMOGRAPHIC SCANNER FOR IMAGE GUIDED INTERVENTIONAL PROCEDURES

BACKGROUND OF THE INVENTION

The present invention relates to the art of interactive image-guided surgery. It finds particular application in conjunction with minimally invasive stereotactic surgery performed in CT imaging systems using a frameless mechanical arm device to guide surgical tools such as biopsy probes or the like and will be described with particular reference thereto. It is to be appreciated, however, that the invention is also applicable to a wide range of imaging equipment and minimally invasive stereotactic surgery procedures including, for example, ultrasonic and magnetic resonance imaging devices and surgery performed using those devices.

Heretofore, several systems have been proposed combining mechanical arm type mechanisms together with human anatomy imaging devices for performing certain interventional surgical procedures such as, for example, the placement of catheters, drainage tubes, biopsy probes, or the like, within a patient's body. U.S. Pat. No. 5,142,930 teaches a mechanical arm device associated with imaging system generating one or more images of a patient's anatomy and displaying those images on a screen. A computer is used to track the location of a surgical tool connected to the mechanical arm as the arm is moved through physical space. The computer performs a transforming rotation of the physical space to the image space in order to cause the display device to show the location of the surgical tool within the patient's image space. Position feedback devices are arranged at each joint of the mechanical arm to detect rotation and angular movement of the arm segments for tracking the end tip of a tool on the arm relative to the position of fiducial implants disposed on or in the patient's body.

One disadvantage of the above system, however, is the need for a bulky stereotactic localization frame. Although the system proposed above tracks the position of the tool carried on the arm relative to the arm's base member, the use of fiducial implants remains necessary to initialize a mapping transformation between the internal coordinate system of the surgical image and the external coordinate system of the mechanical arm.

A frameless stereotactic tomographic scanner for image-guided interventional procedures that does not rely upon the bulky localization frame or the fiducial implants placed in the patient would reduce the setup time spent before surgery and, in addition, would provide a more accurate and repeatable positioning of the surgical tools or probes into the patient's body.

U.S. Pat. No. 5,622,170 teaches a surgical apparatus for determining the position and orientation of an invasive portion of a surgical probe within a patient's body. A computer associated with that system determines the position and orientation of the invasive portion of the surgical tool by correlating the position of the tool relative to a predetermined coordinate system with a position of a model of the patient's body defined in relation to the predetermined coordinate system. The modeling is accomplished by placing at least three non-collinear reference points on the patient. The reference points may be ink spots, tattoos, radiopaque beads, or fiducial implants on the patient. After the patient is imaged with the fiducial markers in place, the interventionist must place the tip of the surgical probe at each of the reference points on the patient to establish the relationship between the reference points in the model space and their current physical locations in the predetermined coordinate system of the patient space.

It would be desirable to perform image-guided minimally invasive stereotactic surgical procedures without the need for implanting fiducial markers in the patient. In addition, it would be desirable to provide an automatic transformation between a surgical tool in a localizer space and the couch upon which a patient rests in scanner space so that the position of the surgical tool, together with an image of the patient in an image space, can be displayed as a composite view on a display monitor or the like.

SUMMARY OF THE INVENTION

In accordance with one aspect of the present invention, a frameless stereotactic surgical apparatus is provided. The surgical apparatus includes an imaging device defining a system in scanner space. The imaging device is adapted to receive a patient's body thereon and generate patient body image information in image space regarding the patient's body located in the scanner space. A localizer device is provided having, on one end, a base portion mounted in a fixed relationship to the imaging device and, on the other end, a surgical tool guide adapted for selective movement into varied positions adjacent a patient's body disposed on the imaging device. A position transducer associated with the localizer device generates, in a localizer space, tip location information of the free end of the localizer device relative to the base portion of the localizer device.

In accordance with another aspect of the present invention, the transform processor in the frameless stereotactic surgical apparatus is a localizer space to scanner space transform processor adapted to convert the first tip location information in the localizer space to converted tip location information of the free end of the localizer device in the scanner space.

In accordance with yet another aspect of the present invention, the imaging device of the frameless stereotactic surgical apparatus is adapted to generate localizer tip position information in the image space based on the first converted tip location information in the scanner space.

Still further, in accordance with yet another aspect of the present invention, the imaging device includes a display unit for simultaneously displaying the patient body image information in the image space together with the localizer tip position information in the image space on a human readable display monitor.

Still yet further, in accordance with yet another aspect of the present invention, the position transducer is adapted to continuously generate the first tip location information as the localizer device is moved along an arbitrary path. The localizer space to scanner space transform processor continuously converts the first tip location information in the localizer space to first converted tip location information in the scanner space as the localizer device is moved along the arbitrary path. The imaging device continuously generates the localizer tip position information in the image space as the localizer device is moved along the arbitrary path. Lastly, the display unit continuously displays the localizer tip information, as the localizer tip information is generated, together with the first patient body image information, on the human readable display monitor.

According to yet another aspect of the present invention, the calibration phantom is provided for calibrating the frameless stereotactic arm to the imaging device using a plurality of imagable touch point sites arranged in at least three dimensions in the localizer space and in the scanner space.

Still yet further in accordance with another aspect of the present invention, the frameless stereotactic surgical apparatus includes an overhead track assembly defining a plurality of fixed positions relative to the imaging device. The localizer device is movable relative to the track assembly and is adapted for selective locking engagement with the track assembly at respective ones of the plurality of fixed positions.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
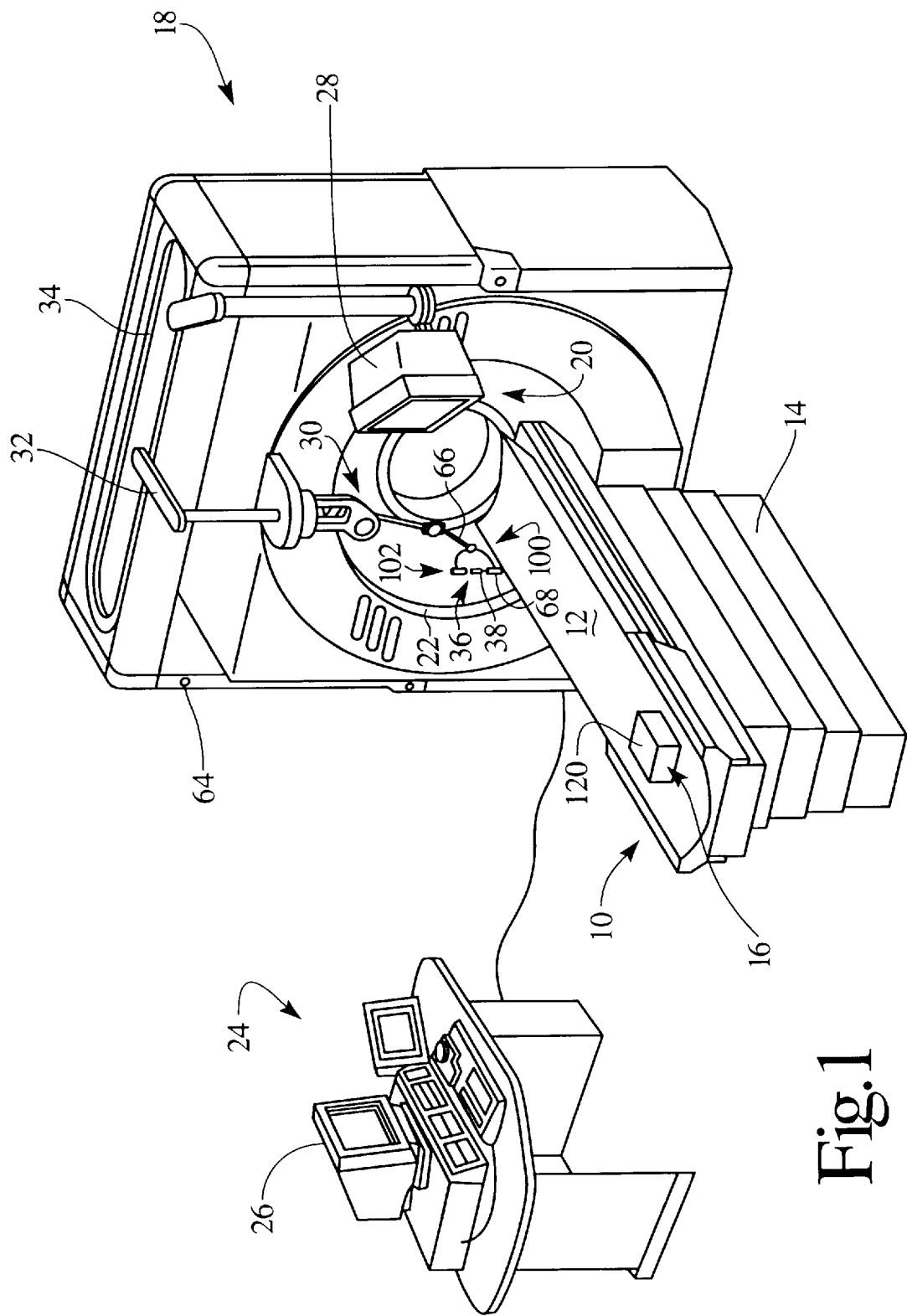
FIG. 1 is a diagrammatic illustration of a frameless stereotactic scanner system including an arm apparatus for image guiding surgical instruments in accordance with the present invention.

Referring now to the drawings wherein the showings are for the purposes of illustrating the preferred embodiments of the invention only and not for purposes of limiting same, with reference first to FIG. 1, a patient table or support 10 includes a patient supporting surface 12 that is mounted for longitudinal movement relative to a base portion 14. The base portion 14 includes a motor for raising and lowering the patient support surface 12 and for moving the patient support surface longitudinally. Position encoders are also provided for generating electrical signals indicative of the height and longitudinal position of the patient support. The patient support includes a calibration and verification area 16 disposed at a known, fixed location. The calibration and verification area is adapted to receive a calibration phantom for calibrating the system in accordance with the present invention and in a manner subsequently described.

A planning, preferably a volumetric diagnostic imaging apparatus 18 is disposed in axial alignment with the patient table such that a patient or subject on the patient support surface 12 can be moved into and through a bore 20 of the volumetric imager. In the illustrated embodiment, the volumetric imager is a CT scanner which includes an X-ray tube mounted for repeated circular travel within a preselected plane. The X-ray tube projects a fan-shaped beam of radiation through a ring 22 of radiation translucent material, through the patient support 12, through a region of interest of the subject, and to a ring or arc of radiation detectors positioned opposite the X-ray tube. As the X-ray tube rotates within the plane, a series of data lines are generated, which data lines are reconstructed into at least a slice image by a reconstruction processor included in a control console 26. The control console is typically remotely located in a shielded room adjacent the scan room. More specifically to the preferred embodiment, the patient support 12 moves longitudinally as the X-ray tube is rotating around the subject such that a selected volume of the patient is scanned along a spiral path or a series of slices. The position of the X-ray tube is monitored by a rotational position encoder, and the longitudinal position of the patient support is monitored by a longitudinal position encoder within the table 10. The reconstruction processor reconstructs a volumetric image representation from the generated data lines. The control console 24 typically includes one or more monitors 26 and various standard operator input devices such as a keyboard, trackball, mouse, or the like. An interventionist control console 28 is supported from overhead on a track atop the CT scanner.

A mechanical frameless stereotactic arm assembly 30 is supported from overhead by a carriage 32 movable on an oval track system 34 affixed to the top of the volumetric diagnostic imaging apparatus 20 as generally shown. The carriage is preferably lockable in one or more predetermined fixed locations on the oval track so that a minimally invasive surgical instrument 36 carried on an interchangeable surgical instrument guidance device 100 formed in accordance with the present invention can be positioned in monitored positions and orientations by an interventionist in preparation for and in carrying out a surgical procedure. The surgical instrument illustrated in the FIGURE includes a laser guided biopsy needle 38 carried by a combined laser and cannula guidance device 102. Overall, however, the position and orientation of the guidance device and the surgical instrument carried thereon are determined by the position of the mechanical arm assembly 30 and the location of the carriage 32 on the oval track system 34.

Figure 2:
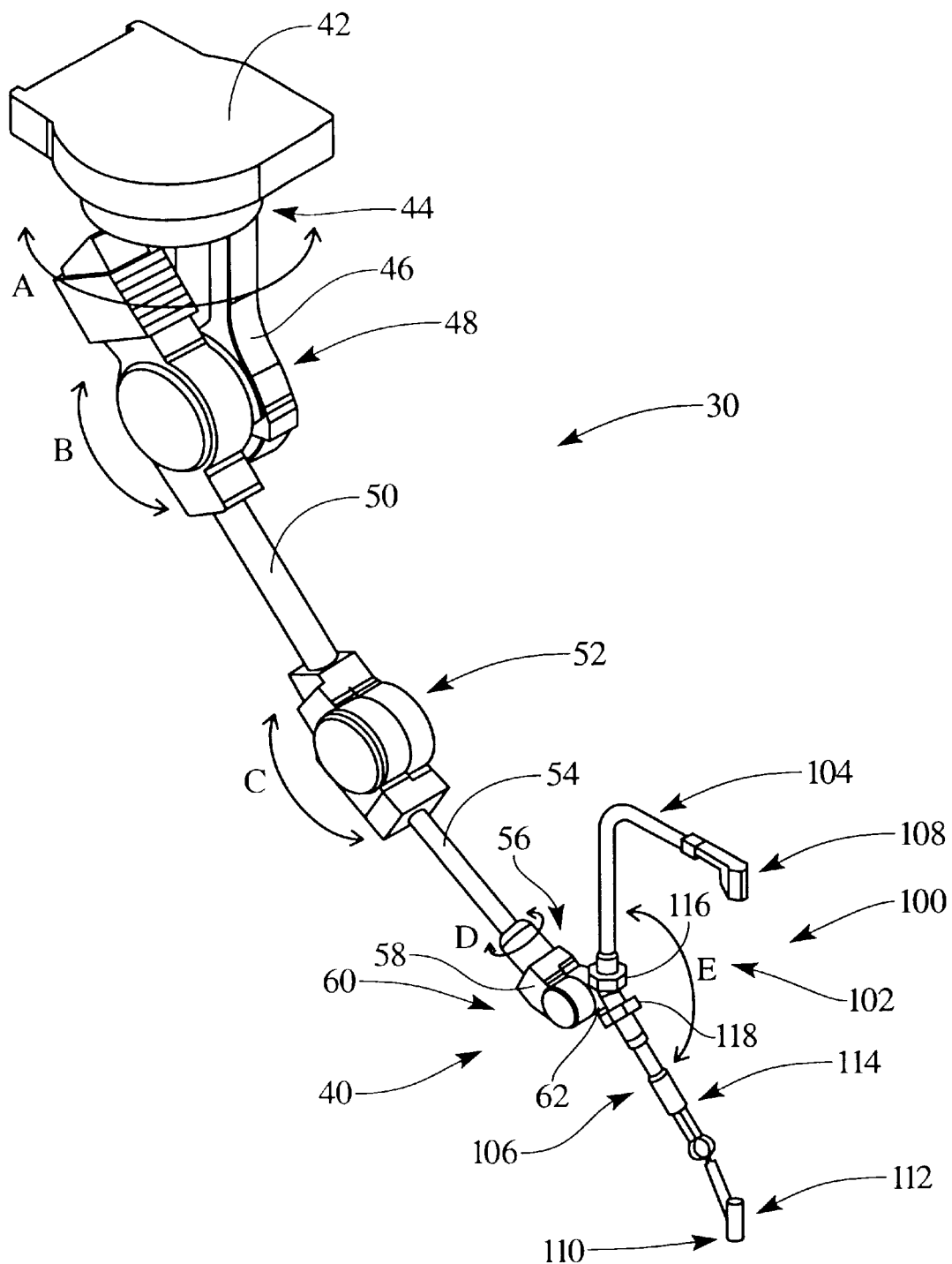
FIG. 2 is a perspective view of the frameless mechanical arm assembly carrying a guidance device formed in accordance with the present invention.

The frameless stereotactic arm assembly 30 is shown generally in FIG. 2 and includes a plurality of arm segments which are interconnected by pivot members forming joints between the arm segments. In that way, a free end 40 of the arm is selectively movable in multiple orientations as necessary to position the surgical instrument 36 into various desired positions over the patient support 12. A base member 42 is rigidly connected to the carriage 32 using suitable fasteners, epoxies, or the like. A base joint 44 permits rotation of a primary support member 46 in a direction marked A. similarly, from the immovable base end of the arm, a shoulder joint 48 permits rotation of an upper arm member 50 in a direction marked B, an elbow joint 52 permits rotation of a lower arm member 54 in a direction marked C, a forearm joint 56 permits rotation of a knuckle member 58 in a direction marked D, and, lastly, a wrist joint 60 permits rotation of a wrist member 62 in a direction marked E.

In accordance with the present invention, at least one position resolver, preferably an optical incremental encoder, is provided at each joint of the mechanical arm assembly 30 to monitor increment articulation and rotation of the arms relative to each other for reasons that will subsequently become apparent. The optical incremental encoders generate feedback pulses indicative of the relative angular and rotational position of the various arm members with respect to each other in a well known manner. The feedback pulses are carried back to an imaging apparatus control circuit using suitable wires or flexible shielded cables extending through the multiple members of the arm assembly. In that way, the position and orientation of the wrist member 62 with respect to the imaging apparatus reference frame and the volumetric image representation obtained by the imaging apparatus.

The position and orientation of surgical instruments carried by the arm assembly relative to the imaging apparatus reference frame and the volumetric image representation obtained by the imaging apparatus are resolved by providing interchangeable surgical instrument guidance devices 100 having a unique identification signal. The identification signal is used by the imaging apparatus control circuit to index a look up table for retrieving various physical dimensional and other functional parameters corresponding to the one or more guidance devices connected to the wrist member 62. In this manner, the physical dimension and other functional parameters, together with the mechanical interconnection which is measured by the resolvers and encoders, provides an accurate indication of the position and orientation of the guidance device 100 relative to the CT scanner and, hence, relative to the image acquired by the CT scanner.

Figure 3:
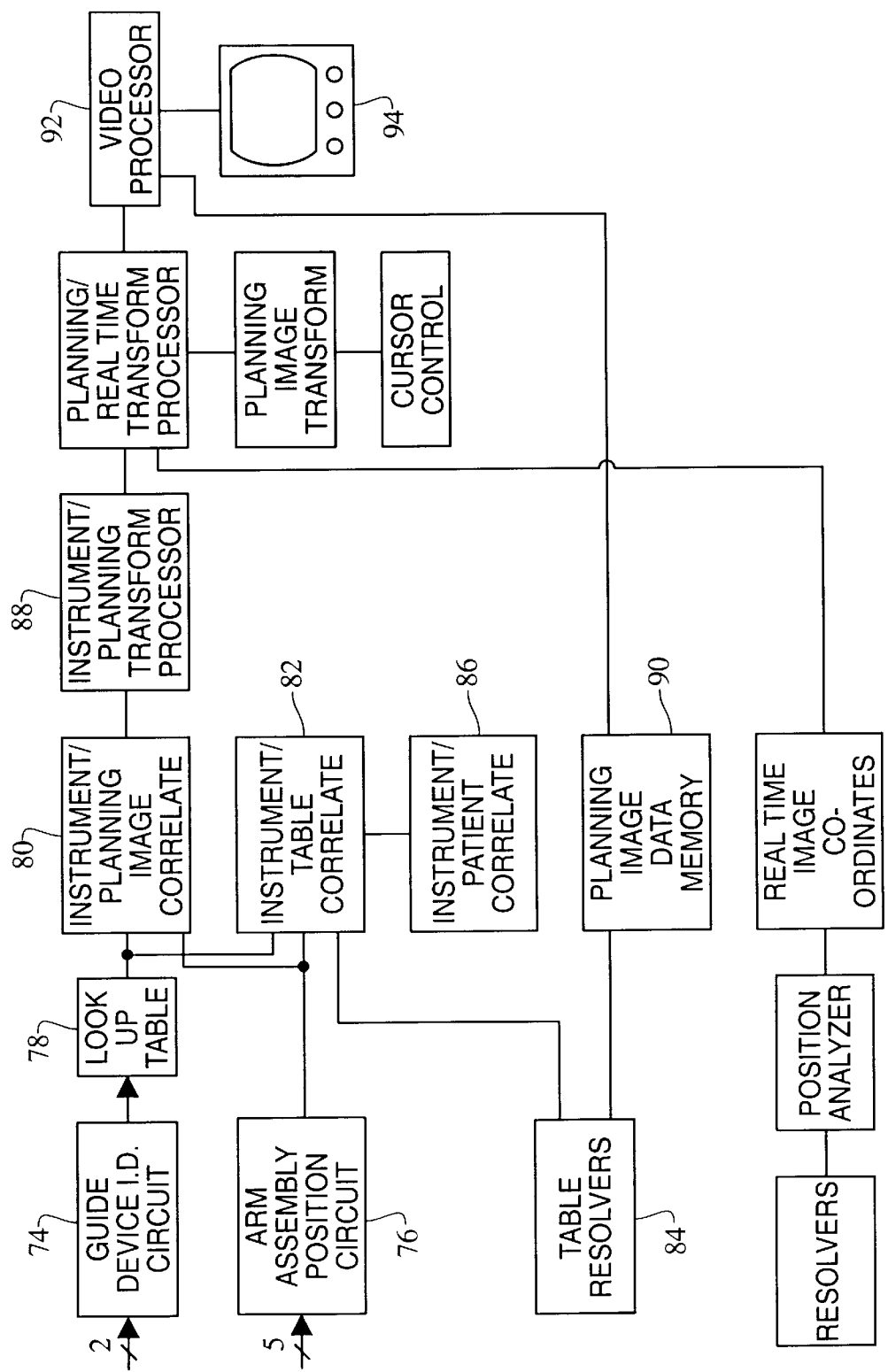
FIG. 3 is a diagrammatic illustration of the planning image processing performed with the apparatus of FIG. 1.

With reference now to FIG. 3, an instrument coordinate circuit 72 determines the position and trajectory of the surgical instrument 36 in instrument space, particularly a coordinate system of the instrument. The instrument coordinate circuit includes a guidance device identification circuit 74 and a mechanical arm assembly position circuit 76. The guidance device identification circuit 74 receives the device identification signal from the one or more guidance devices connected to the mechanical arm and indexes a look up table 78 to retrieve dimensional and functional information. The mechanical arm assembly position circuit 76 is connected with the increment resolvers on the mechanical arm assembly 30 to receive signals indicative of changes of position and orientation of the mechanical arm in instrument space. An instrument-planning scanner correlating processor 80 determines the correlation or transform between the surgical instrument 36 and the volumetric scanner 18 coordinate systems. The correlation or transform is normally described in terms of offset, particularly offset along the axis of the patient support, angular offset or rotation, and scaling.

In the preferred embodiment, a calibration instrument such as a precision localizer device 103 is touched to a set of spaced apart markers, preferably eight, which are disposed in a known relationship to the volumetric scanner coordinate system. The markers are preferably in the form of a calibration phantom 120 located in the calibration marker area 16. By measuring the coordinates of the calibration instrument in the instrument coordinate system while touching each marker, eight or more common points in the two coordinate systems are determined. By determining a barycenter or other characteristic of the common points, but preferably a difference between the centroids of the common points, the offset between the two coordinate systems is determined. By determining the angular difference between the rays from the barycenter to each point in each coordinate system, the angular offset is determined. By determining a difference in physical displacement between the barycenter and the corresponding points in each coordinate system, the scaling factor is determined.

In accordance with the present invention, the localizer device and the volumetric scanner are mechanically linked. Therefore, the transform or relationship between the volumetric scanner and the instrument coordinate system needs only to be calibrated once and, thereafter, is predetermined from the mechanical interconnection between the component parts. The touching of the markers need only be performed once and subsequently used merely to confirm that the instrument and the CT scanner coordinates have not become misaligned between interventional procedures.

Using analogous mathematics or known mechanical relationships as above, an instrument to patient table correlating processor 82 determines the correlation or transform between the patient table and the surgical instrument. Preferably, the calibration phantom described above having the plurality of markers is positioned in a known repeatable position on the table to provide a large number of corresponding points in both coordinate systems for the correlating process. Images of the calibration phantom 120 are utilized to derive transforms between patient table space and planning or real time image coordinate systems.

Table resolvers 84 located in the patient table contribute vertical and longitudinal offsets to the correlation between the surgical instrument and the patient table when the table is raised or lowered and when the patient support 12 is moved axially. An instrument to patient correlation processor 86 determines a correlation between the surgical instrument system and a patient coordinate system. This may be done to provide reassurance to an interventionist by placing the surgical instrument on three or more known references points on the patient. Such points might include readily identifiable anatomical structures such as the tip of the nose, distinctive points of bones, fiducial markers that are aligned during the volumetric imaging process, or the like.

In addition to the above, fiducial points on the scanner (e.g., patient support) can be used to verify the accuracy of the point trajectory localizer within the scanner's coordinate system. In the present invention, the patient is movable in conjunction with the patient support (i.e., couch) while maintaining the registration between the localizer, display, and patient volume data set by resolving and reporting the position of the couch to a display sub-system. The resolved movements of the couch are into and out of the carriage (z-axis) and patient support height (y-axis). The patient support position is digitized and feedback to the display system where adjustments are made to maintain the registration.

The equations for patient support movements are as follows: Let the distance of the first image (i.e., reference image, maximum z value along the patient support) from the aperture (z-0 in scanner coordinates) along the z-axis be represented by > D max z image from aperture=(P[z] max z image pt support −P[z] present pt support).

Then the equation for the transformations for patient support movements are as follows:

> Localizer Tip [z]=Localizer Tip scanner coord[z]−D max z image from aperture where P[z] is the patient support position in the z axis. A similar equation can be written for the patient support movements along the y axis.

If the reference image is in the aperture, then

D max z image from aperture=0 and

Localizer Tip [z]=Localizer Tip scamercoord [z]

Thus, if the localizer has a z value in scanner coordinates which is the same as the reference image, then D max z image from aperture=Localizer Tip scawner coorc [z]

and

Localizer Tip [z]=0 which is the z-axis origin of the image space.

Patient restraint mechanisms (not shown) can be used in order to prevent gross movements of the patient relative to the patient support.

An instrument to volumetric image coordinate system transform processor 88 receives the correlation or transform from the surgical instrument to planning image processor 80. The instrument to volumetric image processor operates on input position and orientation coordinates in image space to transform them into volumetric image data space and visa versa. Knowing the position of the surgical instrument in volumetric or planning data space enables the instrument position and orientation to be superimposed on the volumetric planning image data.

During a medical procedure, the patient is positioned in the volumetric planning scanner and a volumetric image is generated. The volumetric image is stored in a volumetric or planning data memory 90. The position of the patient table during the generation of the planning data, particularly as the table moves to generate spiral or slice data, is stored in conjunction with the volumetric planning data such that the data is correlated with the patient table coordinate system. The operator control 24 controls the volume planning image data memory or a video processor 92 such that selected slices, projection images, surface renderings, or other conventional displays of the data are generated for display on a planning image display 94. Preferably, the planning image display includes corresponding sagittal coronal axial and oblique slices through a common point of intersection.

Because the planning image display is generated before the surgical procedure, the planning movement of the surgical instrument is preferably displayed in the planning image on the interventionist control console 28. The coordinates and trajectory of the surgical instrument are conveyed by the instrument to planning image transform processor 88 for conversion into the planning image coordinate system. The location and trajectory of the instrument in the planning image coordinate system is communicated to the video processor 92 which superimposes the surgical instrument position and trajectory on the CT data display. The mechanical arm assembly generates information that is converted to cursor position signals and virtual needle displays which are transformed into the planning image coordinate system 94 and communicated to the video processor 92 to generate a movable cursor point and a virtual needle representation on the planning image display 94. Preferably, the cursor is positioned at the point of intersection of concurrently displayed transverse, coronal, and sagittal views on the volumetric image display 94. As the operator moves the cursor control 28 through volumetric image data space or as the surgical instrument 36 on the mechanical arm assembly 30 is moved over target areas on the patient, the sagittal, coronal, and transverse views on the interventionist control console 28 change correspondingly.

Figure 4:
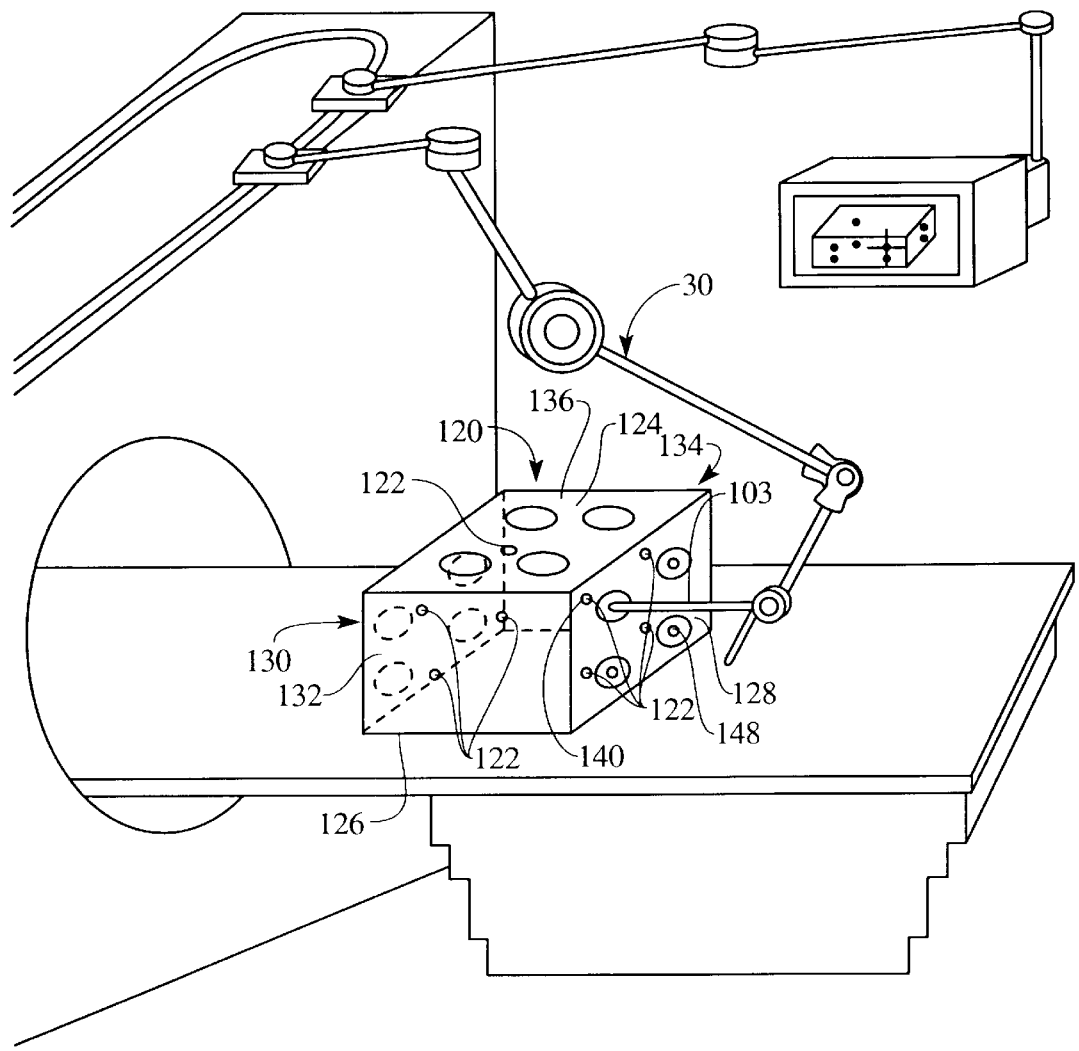
FIG. 4 is a perspective view of a locator device engaged with a calibration phantom in accordance with the present invention.

FIG. 4 illustrates the preferred embodiment of the verification and calibration phantom 120 formed in accordance with the present invention. With reference now to that FIGURE, the phantom 120 includes a plurality of X-ray imagable markers 122 supported in a three dimensional spaced apart relationship by an X-ray opaque phantom body member 124. Preferably, the markers 122 comprise eight precision ground ball bearings formed of stainless steel or regular high carbon steel suitable for medical use. The phantom body 124 is preferably formed of a clear acrylic plastic in the shape generally as shown including a flat bottom surface 126 adapted to engage the scanner table 12 at a repeatable predetermined position in the calibration and verification area 16 described above. In addition, the phantom body includes a front and back side 128, 130, left and right sides 132, 134, and, lastly, a top side 136. Each of the markers 122 are disposed in the calibration phantom 130 in a manner substantially as shown to provide adequate separation between the markers in all three orthogonal axes of the imaging apparatus (x, y, z) in order to ensure accurate and complete three dimensional calibration thereof. In that regard, each of the markers are separated from each other within the phantom body by approximately six (6) inches.

A specialized manually positionable localizer device 103 is illustrated attached to the free end of the mechanical arm assembly 30. The localizer device includes a hardened probe tip 104 which, as illustrated, is substantially circularly cylindrical in cross section and including, on an extreme end thereof, a precision ground flat contact face 106.

Figure 5:
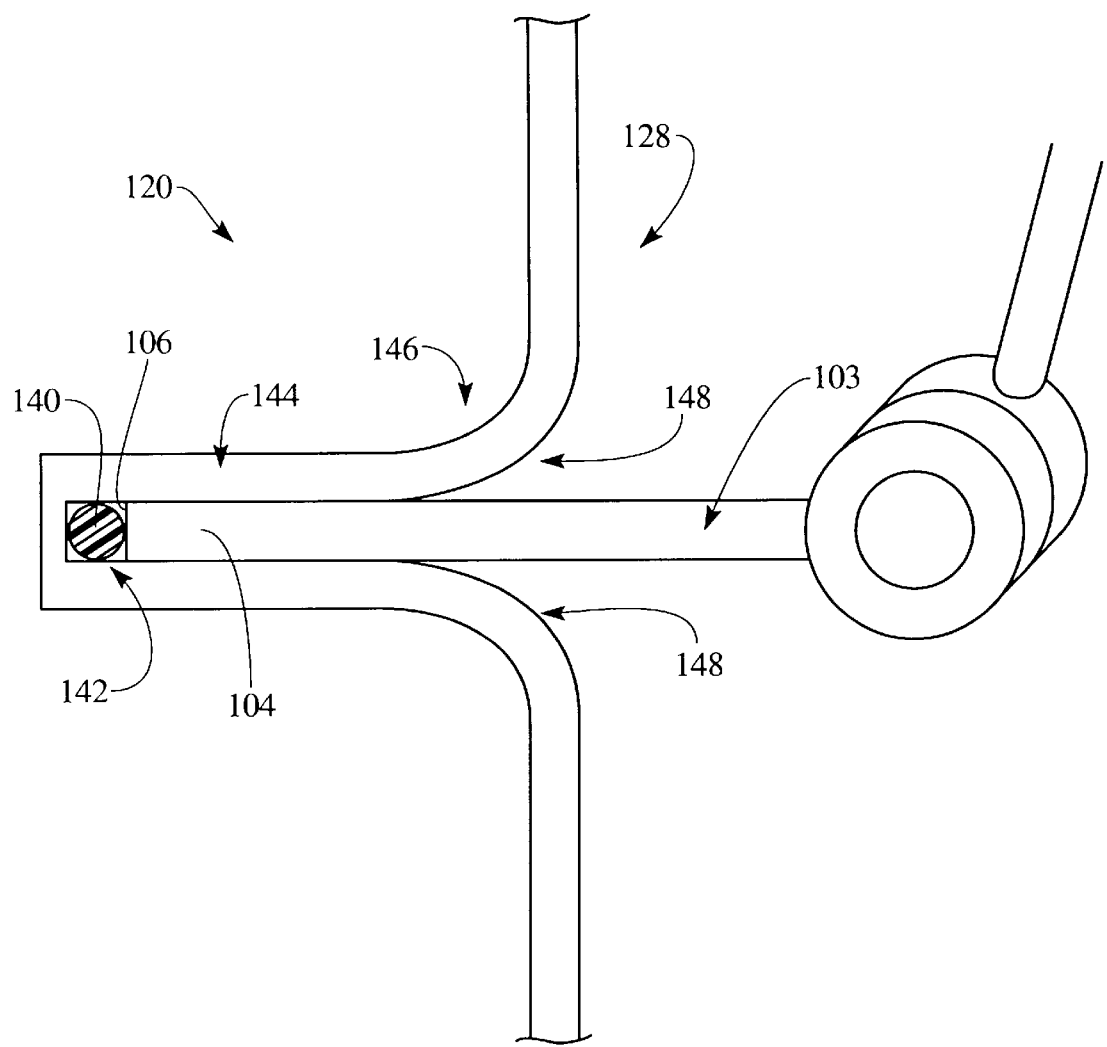
FIG. 5 is a view of a portion of the calibration phantom of FIG. 4 shown in cross section.

With continued reference to FIG. 4, the localizer device 103 is shown engaged with a first calibration marker 140 disposed in a top left corner of the calibration phantom. In order to ensure that the localizer device is properly oriented with respect to the orthogonal axes of the imaging device, access to the plurality of markers within the calibration phantom are restricted by corresponding sets of probe tip guide surfaces 142. In that regard, FIG. 5 illustrates a representative probe tip guide surface formed in accordance with the present invention.

Turning now to that FIGURE, the top left marker 140 is received within a pocket 144 formed on the front side 128 of the calibration phantom 120. An alignment area 146 is provided adjacent the pocket region 144 in a manner substantially as shown. The alignment area 146 is substantially circularly cylindrical in inner diameter cross section and, further, is adapted in size and shape to substantially correspond with the circularly cylindrical cross sectional outer diameter of the probe tip 104 on the localizer device 103. The inner diameter is formed a precise parallel relationship with one of the major axes of the imaging device and in a precise perpendicular relationship with the remaining other major axes of the imaging device. In that way, the alignment area 146 acts to orient the localizer device into alignment with the major orthogonal axes of the imaging device 18.

A small tapered lead-in surface 148 is provided between the alignment area 146 and the front side 128 of the calibration phantom. The lead-in surface may take on any shape but, preferably, is smoothly tapered so that the contact face 106 of the probe tip 104 can be easily guided toward and then into engagement with the top left marker 140. In the above description, although a single marker was described, the description thereof is equally applicable to the other markers 122 disposed in the phantom body 128 and, although only the alignment area 146 and lead-in surface 148 of a single probe tip guide surface 142 was described, the description thereof is equally applicable to the other guide surfaces disposed on each of the front, back, left, right, and top sides of the calibration phantom 120.

Figure 6:
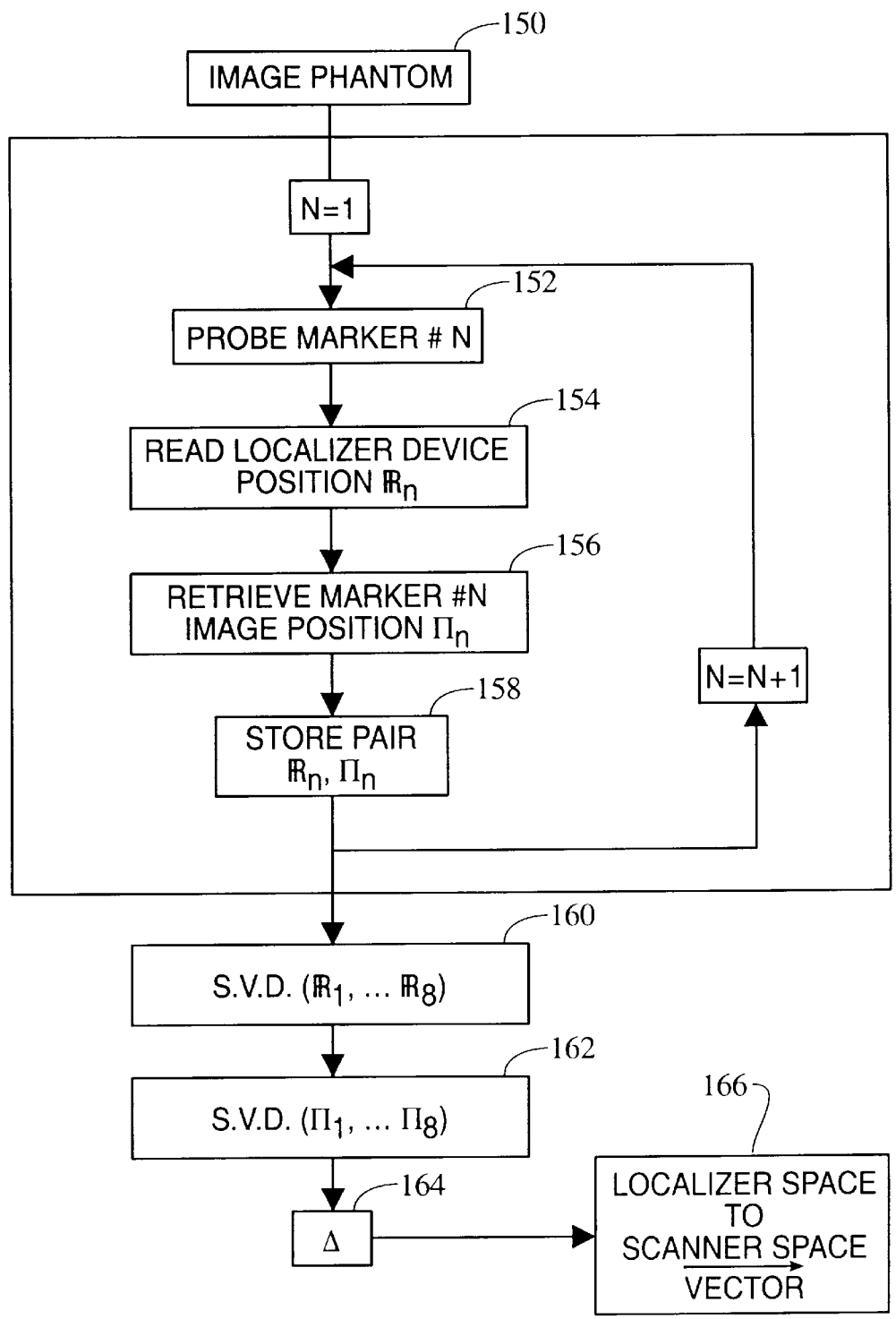
FIG. 6 is a flow chart of a preferred method for calibrating the mechanical arm of the frameless stereotactic tomographic scanner system shown in FIG. 1.
Figure 7:
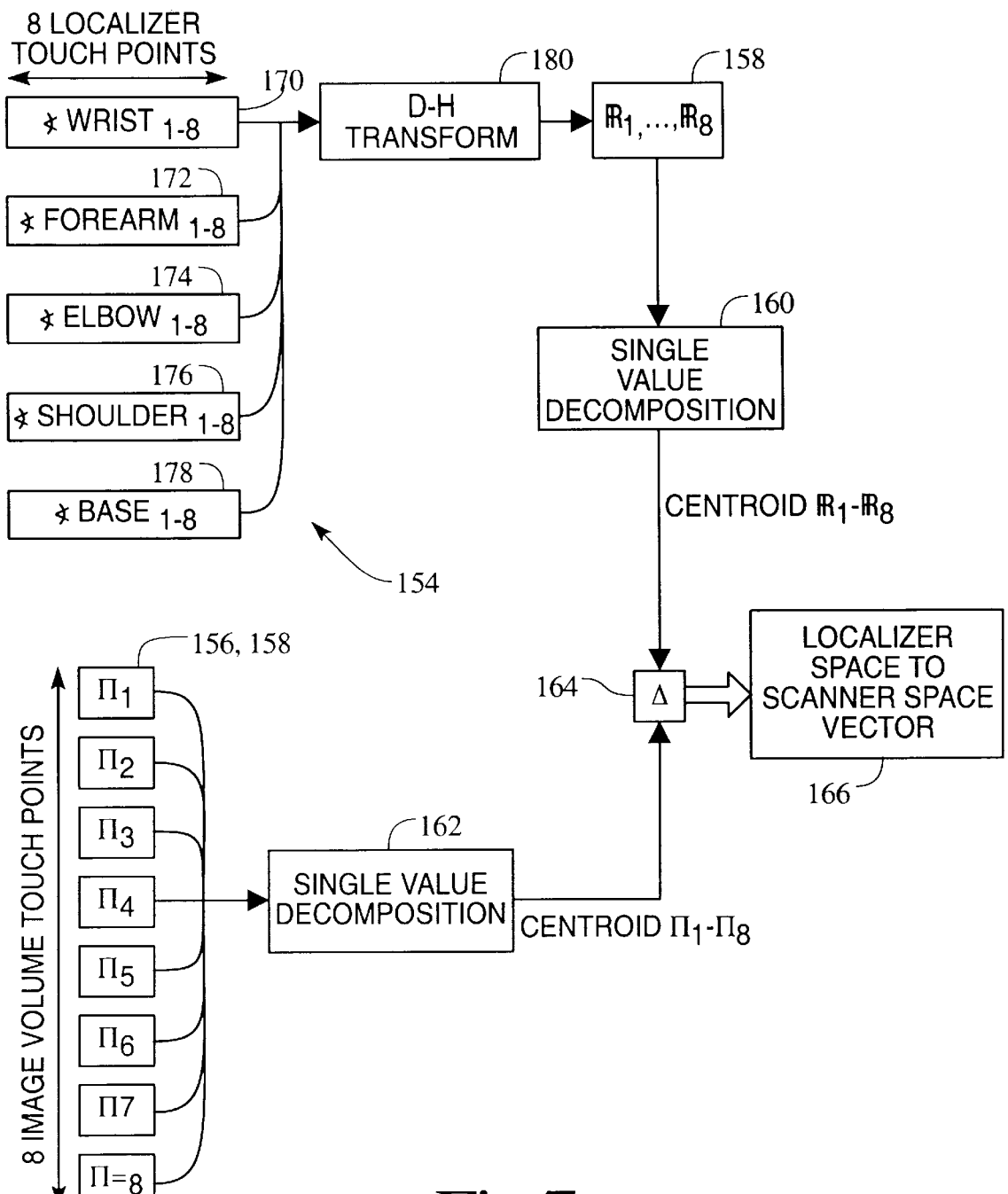
FIG. 7 is a schematic illustration of the method shown in FIG. 6.

Turning now to FIGS. 6 and 7, the preferred method of calibrating the stereotactic arm 30 to the imaging device 18 will be described. The method includes, at a first step 150, imaging the calibration phantom 120. The image of the phantom is stored in the image volume data set 90 (FIG. 3). Next, each of the plurality of markers 122 are probed using the localizer device 102 to derive a set of localizer tip position coordinate information in localizer space $\mathbb{R}$ and a corresponding set of marker image location information in scanner space H.

After imaging the phantom in step 150, the first marker is probed at step 152. In order to probe the first marker, a service technician first must find each of the markers within the phantom body 124 and then engage the contact face 106 of the localizer device 102 to the markers 122 disposed in the phantom body, one at a time, in a manner substantially as shown in FIG. 4. While the contact face is in engagement with each of the markers, a button, switch, or other suitable feedback device on the operator's console 28 is actuated to read, at step 154, the position of the localizer device in localizer space $\mathbb{R}$.

The localizer position in localizer space $\mathbb{R}$ is derived substantially in a manner as shown in FIG. 7. In that regard, upon actuation of the suitable switch mechanism on the operator panel, the angular position of each of the joints of the mechanical arm assembly are interrogated to obtain their position values. More particularly, the wrist, forearm, elbow, shoulder, and base optical position encoders are accessed in step 154 to retrieve their respective encoder count values 170–178 respectively. The count values are easily translated into angular values using well known techniques. A Denavit-Hartenberg transform 180 is implemented to convert the multiple angles of the stacked series of mechanical arm members into a single coordinate point value in localizer space $\mathbb{R}_1$. Similarly, the position of the marker 140 engaged with the contact face 106 is derived in scanner space Π 156. The position of the localizer device in localizer space $\mathbb{R}$ and the position of the marker in scanner space Π are stored in a temporary memory at step 158.

The steps described above are repeated for each of the plurality of markers 122 disposed in the body 124 of the calibration phantom 120. According to the preferred embodiment of the instant invention, the steps are repeated eight times, once for each marker.

After each of the pairs of localizer tip positions in localizer space $\mathbb{R}$ and marker positions in scanner space Π are collected, a single value decomposition process 160 is performed on the set of localizer tip information in Vocalizer space $\mathbb{R}$. Similarly, a single value decomposition is performed, at step 162, on the set of marker locations in scanner space Π. The single value deposition of the set of localizer device positions in localizer space results in a centroid 182 in localizer space $\mathbb{R}$. Similarly, the single value decomposition of the set of marker coordinates in scanner space result in a centroid 184 in scanner space Π. A difference calculation is performed at step 164 between the centroid in localizer space 182 and the centroid in scanner space 184. The resultant difference is a localizer space to scanner space vector 166. The vector is stored in a suitable memory location within the imaging device for use in translating localizer space coordinates to scanner space coordinates for the display of patient image data and mechanical arm image data on the operator and display panel 28 as the arm is moved adjacent the patient in a manner substantially as described above.

Figure 8:
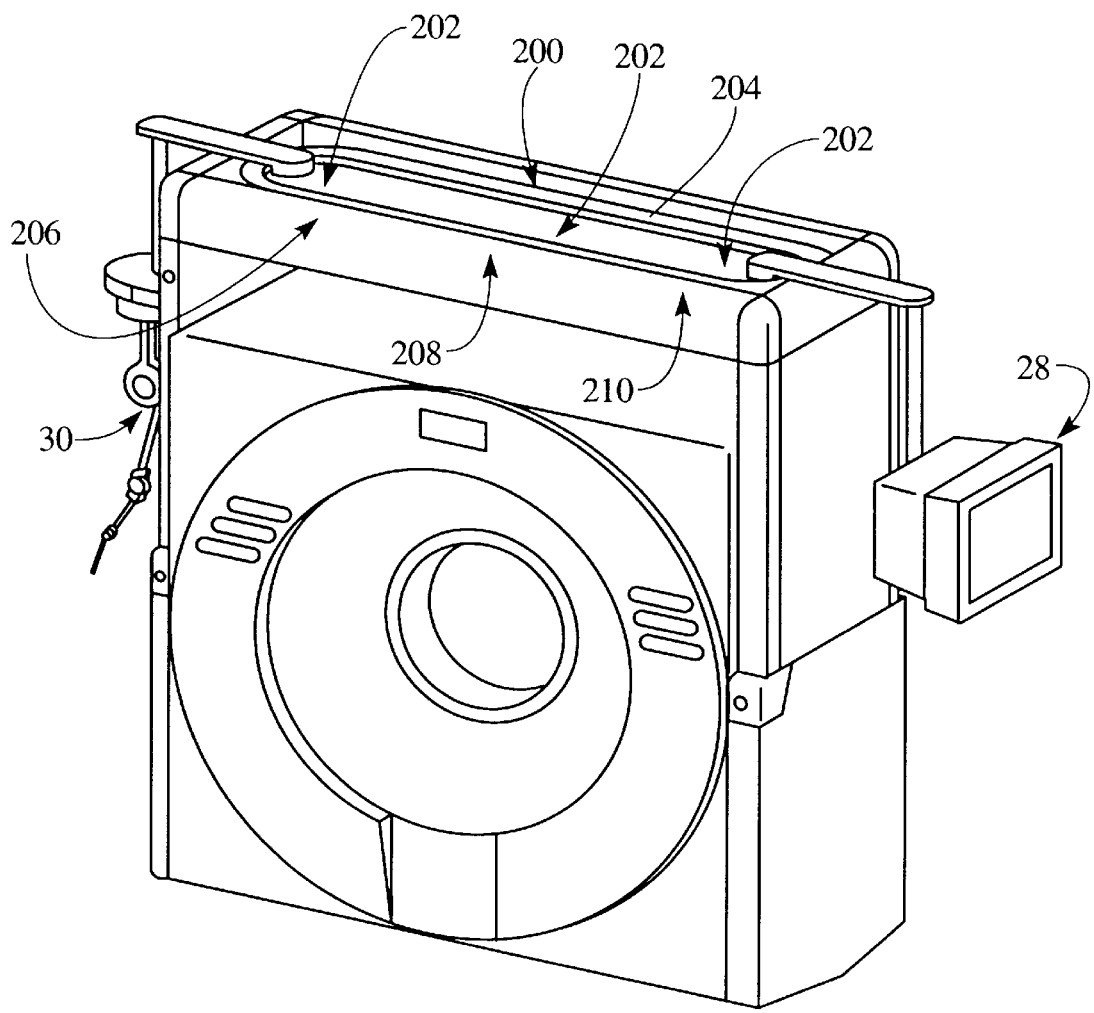
FIG. 8 is a perspective view of the frameless stereotactic arm assembly and interventionist control panel supported from overhead in a parked position on the CT scanner in accordance with the present invention; and, FIG. 9 is a view in cross section of the mechanical arm carriage and a locking mechanism formed in accordance with the present invention.
Figure 9:
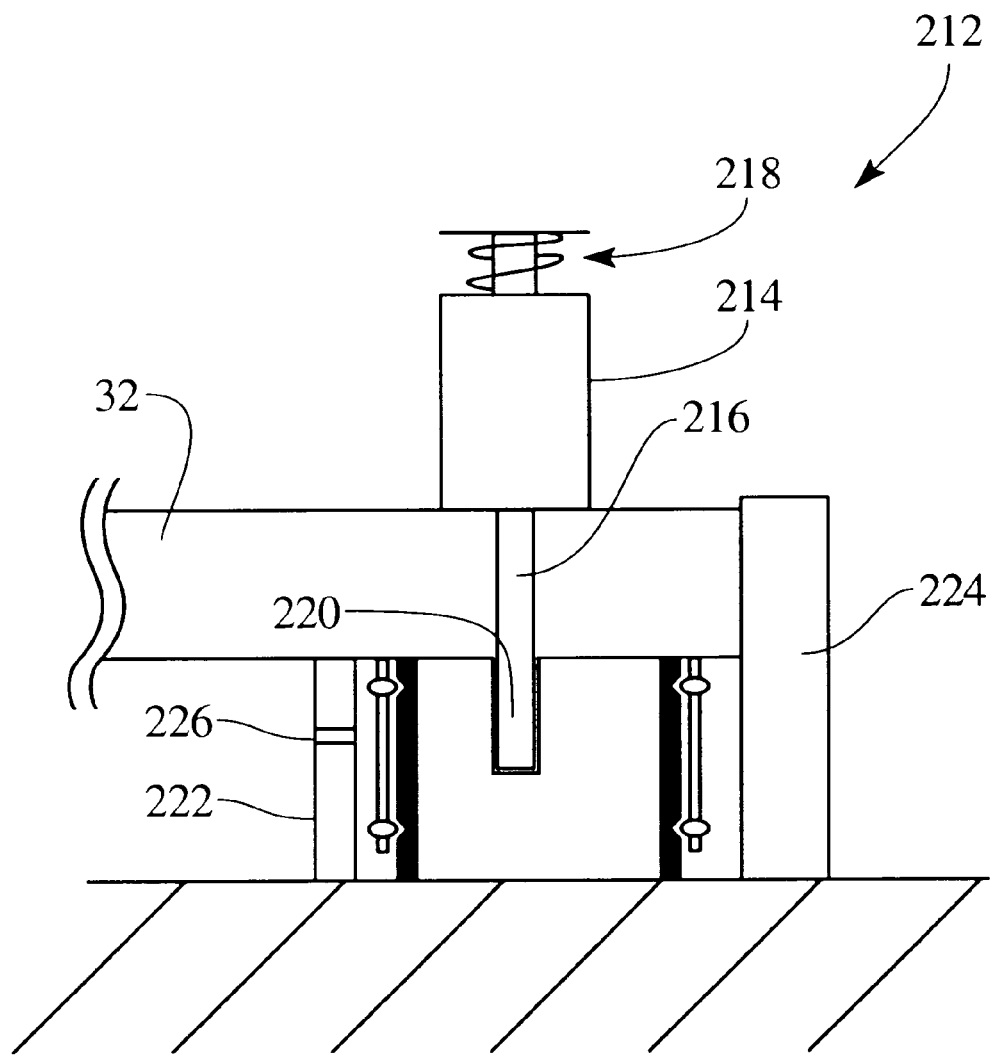

Turning now to FIGS. 8 and 9, and also, with reference to FIG. 1, the imaging apparatus 18 includes an overhead carriage support track 200 adapted to support the stereotactic arm assembly 30 and the interventionist control panel from overhead and conveniently off of the scanner room floor. The carriage support track provides a set of detent positions 202 for the mechanical arm assembly along a generally oval track 204 which, in its preferred construction, is rigidly attached to the top of the imaging device as shown. The detent positions include a left 206, center 208, and right 210 detent positions whereat a locking mechanism 212 engages the track 204 to rigidly locate the mechanical arm assembly at predetermined repeatable positions along the face of the imaging device. FIG. 1 shows the mechanical arm assembly at the center 208 position. FIG. 2 shows the mechanical arm assembly 30 and interventionist display and control panel 28 in their parked positions. In accordance with the present invention, the imaging apparatus includes an interlock circuit (not shown) to enable x-ray imaging of specimens only when the overhead apparatus are arranged as shown in FIG. 8 in the parked position.

Turning more particularly to FIG. 9, the locking mechanism 212 includes an electric solenoid device 214 responsive to commands from the imaging apparatus to move a plunger pin 216 against the force of a spring member 218 out of engagement with a locating hole 220 provided at the left, center, and right detent positions along the track 204. In accordance with the preferred embodiment of the invention, the carriage member 32 of the mechanical arm assembly is adapted to receive the plunger pin 216 therethrough. In that way, accurate and repeatable location of the mechanical arm is achieved. In addition, the track 204 is provided at each of the left, center, and right detent positions with a cam follower rail 222 and a reinforcement back rail 224. The cam follower rail 222 provides additional forward support to the carriage 32 against the torque created by the weight of the mechanical arm assembly. The reinforcement back rail 224 ensures that the carriage is in proper alignment with the three major orthogonal axes of the imaging apparatus 18. Lastly, in connection with the locking mechanism 212 shown in FIG. 9, a magnetic reed switch 226 is provided at each of the left, center, and right detent positions to generate a signal for use by the interlock control circuit of the imaging apparatus described above to indicate the location of the carriage at a one of the detent positions.

Operationally, in order to move the mechanical arm assembly from the parked position illustrated in FIG. 8 to the center detent position 208 illustrated in FIG. 1, an interventionist activates a suitable button or switch on the interventionist control panel 28 whereupon the solenoid device 214 is actuated to withdraw the plunger pin 216 from engagement with the locating hole 220. Suitable wheels, slides, or other low friction interface provided between the track 204 and carriage 32 enables the latter to be moved along the track manually. In accordance with the present invention, however, the carriage 32 is slidably connected to the track 204 using a plurality of opposing precision wheel members 230 supported on the carriage by suitable precision roller bearings or the like. The wheel members are adapted to engage corresponding opposed precision surfaces 232 formed in the track.

The invention has been described with reference to the preferred embodiment. obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A frameless stereotactic surgical apparatus comprising:

an imaging device defining a coordinate system in scanner space Π, the imaging device being adapted to receive a patient body thereon and generate first patient body image information in image space $\mathbb{I}$ regarding the patient body located in said scanner space Π;

a localizer device having a base portion mounted in a fixed relationship to the imaging device and a free end adapted for selective movement into varied positions adjacent the patient body disposed in said scanner space Π;

a position transducer associated with the localizer device to generate, in a localizer space $\mathbb{R}$, first tip location information of said free end of the localizer device relative to the base portion of the localizer device; and, a first transform processor adapted to generate a localizer space to scanner space transform vector based on a difference between a first centroid developed in said localizer space $\mathbb{R}$ and a second centroid developed in said scanner space Π and to convert said first tip location information in said localizer space $\mathbb{R}$ to first converted tip location information of said free end of the localizer device in at least a one of said scanner space Π and said image space $\mathbb{I}$ using said localizer space to scanner space transform vector.

2. The frameless stereotactic surgical apparatus according to claim 1 wherein the first transform processor is a localizer space to scanner space transform processor adapted to convert said first tip location information in said localizer space $\mathbb{R}$ to said first converted tip location information of said free end of the localizer device in said scanner space Π.

3. The frameless stereotactic surgical apparatus according to claim 2 wherein the imaging device is adapted to generate localizer tip position information in said image space $\mathbb{I}$ based on said first converted tip location information in said scanner space Π.

4. The frameless stereotactic surgical apparatus according to claim 3 wherein the imaging device includes a display unit for displaying said first patient body image information in said image space $\mathbb{I}$ together with said localizer tip position information in said image space $\mathbb{I}$ on a human readable display monitor.

5. The frameless stereotactic surgical apparatus according to claim 4 wherein:

the localizer device is adapted to move from a first position near the patient body to a second position near the patient body along an arbitrary path;

the position transducer is adapted to continuously generate, in said localizer space $\mathbb{R}$, said first tip location information as the localizer device is moved along said arbitrary path;

the localizer space to scanner space transform processor is adapted to continuously convert said first tip location information in said localizer space $\mathbb{R}$ to said first converted tip location information in said scanner space Π as the localizer device is moved along said arbitrary path;

the imaging device is adapted to continuously generate said localizer tip position information in said image space $\mathbb{I}$ as the localizer device is moved along said arbitrary path; and, the display unit is adapted to continuously display said localizer tip information, as the localizer tip information is generated, together with said first patient body image information, on said human readable display monitor.

6. The frameless stereotactic surgical apparatus according to claim 1 wherein at least one of the localizer device and the imaging device is adapted to mount the base portion of the localizer device at a plurality of fixed positions on the imaging device.

7. The frameless stereotactic surgical apparatus according to claim 6 wherein:

the imaging device includes an overhead track assembly defining said plurality of said fixed positions; and, the localizer device is movable relative to the track assembly and is adapted for selective locking engagement with the track assembly at respective ones of said plurality of fixed positions.

8. The frameless stereotactic surgical apparatus according to claim 1 further including a calibration phantom adapted for selective mounting in a fixed relationship to the imaging device.

9. The frameless stereotactic surgical apparatus according to claim 8 wherein the calibration phantom is adapted to provide a plurality of imagable touch point sites in at least three dimensions in said localizer space $\mathbb{R}$ and said scanner space Π.

10. A frameless stereotactic surgical apparatus comprising:

an imaging device defining a coordinate system in a scanner space Π, the imaging device being adapted to receive a patient body thereon and generate first patient body image information in an image space $\mathbb{I}$ regarding the patient body located in said scanner space Π;

a localizer device having a base portion mounted in a fixed relationship to the imaging device and a free end adapted for selective movement into varied positions adjacent the patient body disposed in said scanner space Π, the localizer device being selectively movable from a first position near the patient body to a second position near the patient body along an arbitrary path;

a position transducer associated with the localizer device adapted to generate, in a localizer space $\mathbb{R}$, first tip location information of said free end of the localizer device relative to the base portion of the localizer device, the position transducer being adapted to continuously generate, in said localizer space $\mathbb{R}$, said first tip location information as the localizer device is moved along said arbitrary path;

a localizer space to scanner space transform processor adapted to generate a localizer space to scanner space transform vector based on a difference between a first centroid developed in said localizer space $\mathbb{R}$ and a second centroid developed in said scanner space Π and to convert said first tip location information in said localizer space $\mathbb{R}$ to first converted tip location information in at least a one of said scanner space Π and said image space $\mathbb{I}$, the localizer space to scanner space transform processor being adapted to continuously convert said first tip location information in said localizer space $\mathbb{R}$ to said first converted tip location information in said scanner space Π as the localizer device is moved along said arbitrary path;

a display unit for displaying said first patient body image information in said image space $\mathbb{I}$ together with said localizer tip position information in said image space $\mathbb{I}$ on a human readable display monitor, the display unit being adapted to continuously display said localizer tip information as the localizer tip information is generated together with said first patient body image information; and, a calibration phantom adapted for selective mounting in a fixed relationship to the imaging device and providing a plurality of imagable touch point sites in at least three dimensions in said localizer space $\mathbb{R}$ and in said scanner space $\mathbb{I}$.

11. The frameless stereotactic surgical apparatus according to claim 10 further comprising:

means for developing said first centroid in said localizer space $\mathbb{R}$ based on a set of first tip location information generated by said position transducer by positioning said localizer device at said plurality of imagable touch point sites; and, means for developing said second centroid in said scanner space $\Pi$ based on a set of first calibration phantom image information generated by said imaging device by positioning said localizer device at said plurality of imagable touch point sites.

12. A frameless stereotactic surgical apparatus comprising:

an imaging device defining a coordinate system in a scanner space $\Pi$, the imaging device being adapted to receive a patient body thereon and generate first patient is body image information in an image space $\mathbb{I}$ regarding the patient body located in said scanner space $\Pi$;

a localizer device calibrated to the imaging device with a calibration vector and having a base portion mounted in a fixed relationship relative to the imaging device and a free end adapted for selective movement into varied positions adjacent the patient body disposed in said scanner space $\Pi$;

a position transducer associated with the localizer device to generate, in a localizer space $\mathbb{R}$, first tip location information of said free end of the localizer device relative to the base portion of the localizer device; and, a first transform processor adapted to use said calibration vector to convert said first tip location information in said localizer space $\mathbb{R}$ to first converted tip location information of said free end of the localizer device in at least a one of said scanner space $\Pi$ and said image space $\mathbb{I}$.

13. The frameless stereotactic surgical apparatus according to claim 12 wherein the first transform processor is a localizer space to scanner space transform processor adapted to convert said first tip location information in said localizer space $\mathbb{R}$ to said first converted tip location information of said free end of the localizer device in said scanner space $\Pi$.

14. The frameless stereotactic surgical apparatus according to claim 12 wherein the imaging device is adapted to generate localizer tip position information in said image space $\mathbb{I}$ based on said first converted tip location information in said scanner space $\Pi$.

15. The frameless stereotactic surgical apparatus according to claim 14 wherein the imaging device includes a human readable display unit for displaying said first patient body image information in said image space $\mathbb{I}$ together with said localizer tip position information in said image space $\mathbb{I}$.

16. The frameless stereotactic surgical apparatus according to claim 15 wherein:

the localizer device is adapted to move from a first position near the patient body to a second position near the patient body along an arbitrary path;

the position transducer is adapted to continuously generate, in said localizer space $\mathbb{R}$, said first tip location information as the localizer device is moved along said arbitrary path;

the first transform processor is adapted to continuously convert said first tip location information in said localizer space $\mathbb{R}$ to said first converted tip location information in said scanner space $\Pi$ as the localizer device is moved along said arbitrary path;

the imaging device is adapted to continuously generate said localizer tip position information in said image space $\mathbb{I}$ as the localizer device is moved along said arbitrary path; and, the display unit is adapted to continuously display said localizer tip information, as the localizer tip information is generated, together with said first patient body image information.

17. The frameless stereotactic surgical apparatus according to claim 16 wherein the base portion of the localizer device is selectively mountable at a plurality of fixed positions on the imaging device.

18. The frameless stereotactic surgical apparatus according to claim 17 wherein:

the imaging device includes an overhead track assembly defining said plurality of said fixed positions; and, the localizer device is movable relative to the track assembly and is adapted for selective locking engagement with the track assembly at respective ones of said plurality of fixed positions.

19. The frameless stereotactic surgical apparatus according to claim 16 wherein said first transform processor is adapted to generate a localizer space to scanner space transform vector based on a difference between a first centroid developed in said localizer space $\mathbb{R}$ and a second centroid developed in said scanner space $\Pi$.

20. The frameless stereotactic surgical apparatus according to claim 19 further comprising:

means for developing said first centroid in said localizer spacer $\mathbb{R}$ based on a set of first tip location information generated by said position transducer by positioning said localizer device at said plurality of imagable touch point sites; and, means for developing said second centroid in said scanner space $\Pi$ based on a set of first calibration phantom image information generated by said imaging device by positioning said localizer device at said plurality of imagable touch point sites.

* * * * *